United States Patent
Nissilä

(10) Patent No.: US 7,914,418 B2
(45) Date of Patent: Mar. 29, 2011

(54) METHOD AND APPARATUS IN CONNECTION WITH EXERCISE

(75) Inventor: Juuso Nissilä, Ii (FI)

(73) Assignee: Polar Electro Oy, Kempele (FI)

( * ) Notice: Subject to any disclaimer, the term of this patent is extended or adjusted under 35 U.S.C. 154(b) by 83 days.

(21) Appl. No.: 12/421,797

(22) Filed: Apr. 10, 2009

(65) Prior Publication Data

US 2009/0275442 A1    Nov. 5, 2009

(30) Foreign Application Priority Data

Apr. 30, 2008   (FI) ...................................... 20085398

(51) Int. Cl.
*A63B 71/00*   (2006.01)
(52) U.S. Cl. ................. 482/4; 482/1; 482/901; 600/520
(58) Field of Classification Search ................. 482/1–9, 482/900–902; 600/300, 301, 513, 520; 434/247
See application file for complete search history.

(56) References Cited

U.S. PATENT DOCUMENTS

| | | | |
|---|---|---|---|
| 4,281,663 A | 8/1981 | Pringle | |
| 4,898,182 A | 2/1990 | Hawkins et al. | |
| 7,805,186 B2 * | 9/2010 | Pulkkinen et al. | 600/520 |
| 2001/0020135 A1 * | 9/2001 | Heikkila | 600/513 |
| 2005/0038351 A1 * | 2/2005 | Starobin et al. | 600/516 |
| 2006/0032315 A1 | 2/2006 | Saalastic et al. | |

* cited by examiner

*Primary Examiner* — Glenn Richman
(74) *Attorney, Agent, or Firm* — Hoffmann & Baron, LLP (57) ABSTRACT

An apparatus for an interval exercise performable by a person, the interval exercise including at least two training intervals, each including a work phase and a recovery phase, wherein processing a first exercise parameter data characterizing an exertion level of the interval exercise, detecting a work phase of a training interval from the first exercise parameter data, detecting a value of the first exercise parameter from the exercise parameter data at end of the work phase, and determining a threshold level of a physiological parameter, measured from the person and characterizing the person's recovery level in a recovery phase, based on the value of the first exercise parameter at the end of the work phase.

15 Claims, 5 Drawing Sheets

METHOD AND APPARATUS IN CONNECTION WITH EXERCISE

CROSS-REFERENCE TO RELATED APPLICATION

This application claims priority based on Finnish Patent Application No. 20085398, filed Apr. 30, 2008, which is incorporated herein by reference.

BACKGROUND

1. Field

The invention relates to sports, particularly to interval fitness exercises.

2. Description of the Related Art

An interval exercise is an exercise including alternating work phases and recovery phases. In athletics, for instance, the work phase may include the person lifting a certain weight ten times. After the work phase, a recovery phase is held before carrying out the next work phase. The purpose of the recovery phase is to recover the muscles or body optimally, so that recovery from the work phase is sufficient but not too excessive, thereby giving the desired training results.

Usually, time based instructions based on the type of sports are provided for the recovery periods. When training muscular endurance, for instance, the recovery period may be 1 to 1.5 minutes. When training strength, a recovery period of 5 minutes may be applied after each work phase.

Time-based control of the recovery periods has several deficiencies. In practise, the recovery time within which an exerciser truly recovers from an exercise in a manner optimal to the training is dependent on several factors, such as physical condition of the person, tiredness of the person or the strain of the preceding training, for instance. These factors are not taken into account in a simple time-based recovery control.

SUMMARY

In an aspect, there is provided an apparatus for an interval exercise performable by a person, the interval exercise including at least two training intervals, each including a work phase and a recovery phase, the apparatus comprising means for processing a first exercise parameter data characterizing an exertion level of the interval exercise. The apparatus comprises means for detecting a work phase of a training interval from the first exercise parameter data, means for detecting a value of the first exercise parameter from the exercise parameter data at end of the work phase and means for determining a threshold level of a physiological parameter, measured from the person and characterizing the person's recovery level in a recovery phase, based on the value of the first exercise parameter at the end of the work phase.

In another aspect, there is provided a method for an interval exercise performable by a person, the interval exercise including at least two training intervals, each including a work phase and a recovery phase, the method comprising processing a first exercise parameter data characterizing an exertion level of the interval exercise. The method comprises detecting a work phase of a training interval from the first exercise parameter data, detecting a value of the first exercise parameter from the exercise parameter data at end of the work phase, and determining a threshold level of a physiological parameter, measured from the person and characterizing the person's recovery level in a recovery phase, based on the value of the first exercise parameter at the end of the work phase.

BRIEF DESCRIPTION OF THE DRAWINGS

In the following the invention will be described in greater detail by means of preferred embodiments with reference to the accompanying drawings, in which.

DETAILED DESCRIPTION

Figure 1:
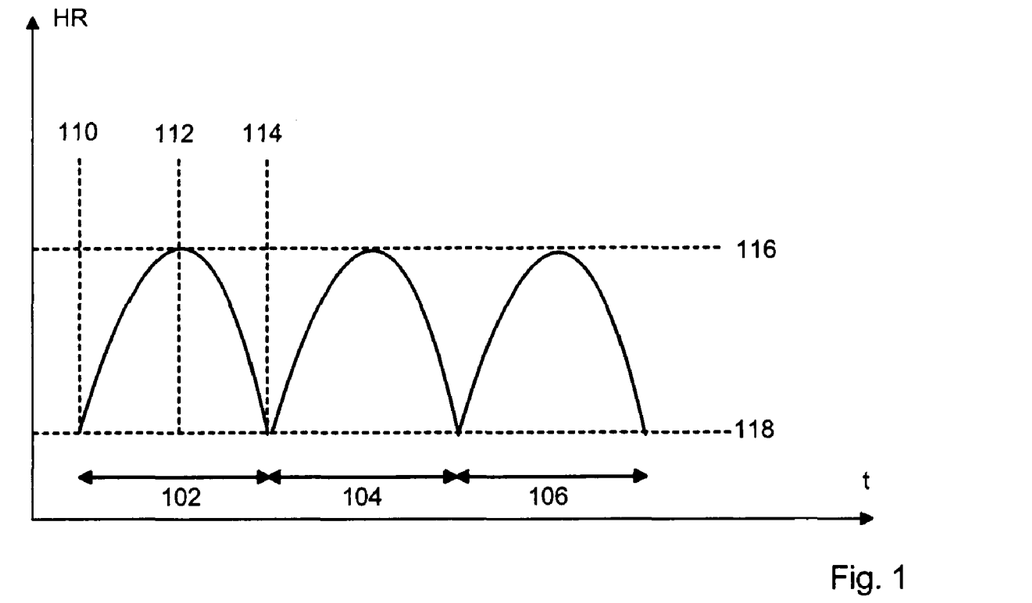
FIG. 1 shows a heart rate graph in an interval exercise.

FIG. 1 illustrates the concepts applicable in conjunction with an interval exercise. In the graph, time "t" is depicted on the x-axis and heart rate "HR" measured from a person carrying out the exercise is depicted on the y-axis. The heart rate in this case exemplifies a parameter characterizing the person's exertion.

The exercise plot in FIG. 1 includes three training intervals 102, 104 and 106. The sections of the interval 102 have been illustrated in more detail. In 110, the first interval starts. At that moment, the person starts lifting weights, running or cycling, for instance. The intensity of the training is such that it causes the person's heart rate to increase. The period between 110 and 112, i.e. what is called a work phase, is finished around 112. Finishing here means that the training is stopped or the intensity of the training is substantially decreased at point 112 compared to the intensity between 110 and 112. After point 112 a recovery phase starts during which the heart rate of the person starts to decrease. At 114, when a predetermined time has lapsed or the heart rate has sunk to the level 118, the person may start the work phase of the second interval 104.

Figure 2:
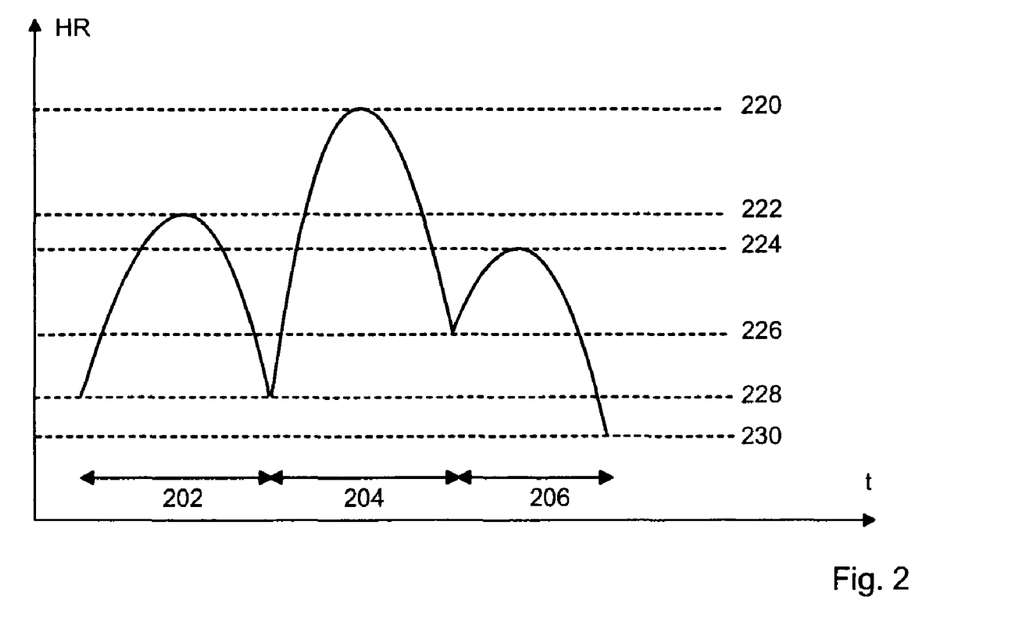
FIG. 2 shows a heart rate graph in another interval exercise.

FIG. 2 illustrates a heart rate plot of another interval exercise having three intervals 202, 204 and 206. The first interval 202 has a normal bell shape, where the heart rate level at the start of the work phase equals to the heart rate level at the end of the recovery period of the first interval 202. However, in the second training interval 204, the person raises the intensity of the interval such that the heart rate goes up to the level depicted by the dashed line 220. At that point, the recovery heart rate level depicted by the line 226 may be calculated from the maximum heart rate level at the end of the work phase of the interval 204. When the heart rate of the person has reached level 226, the third interval 206 may be started. During this interval, the person's heart rate only rises to the level illustrated by line 224. A new recovery threshold level 230 may be calculated based on the level 224.

In FIGS. 1 and 2, a decision procedure may be applied in each interval to determine whether the heart rate has long enough shown a certain trend so as to count as the beginning of a work phase or a recovery phase. In FIG. 1 with regard to the work phase 110-112, the heart rate may increase during a period of 10 seconds, which may trigger a conclusion that a work phase has begun. Similarly, after reaching point 112, the heart rate may be decreasing for 10 seconds, which may be concluded to be an indicator of a recovery period having started.

In FIGS. 1 and 2, the upwards-directing section, that is the work phase of each interval, is not necessarily completely illustrative of the actual exercise carried out by the person.

That is, at the end of the work phase, the heart rate may continue increasing some seconds after the person has finished exercising. The peak of the heart rate curve does not thus necessarily occur exactly at the moment when the person finishes training.

Furthermore, although the shapes of the intervals depicted in FIGS. 1 and 2 have a fairly continuous shape, this is not necessarily the case in practise. For instance in gym training with weights, a person may carry out extra activity during the recovery phases, such as moving weights. Such extra activity may postpone the next work phase timewise as the person's heart rate does not go down as quickly as it would without such activity.

Furthermore, although FIGS. 1 and 2 show the exercise parameter to be heart rate, it may also be some other exercise-related parameter. For instance, during the work phase, a workout parameter may be measured. In weight lifting, the workout parameter may be calculated based on the weight and the number of repetitions, for instance. Such a workout parameter may be converted to a heart rate parameter to be monitored in the recovery phase. Thus, the parameters to be monitored in the work phase and in the recovery phase may be the same but are not necessarily the same.

Figure 3:
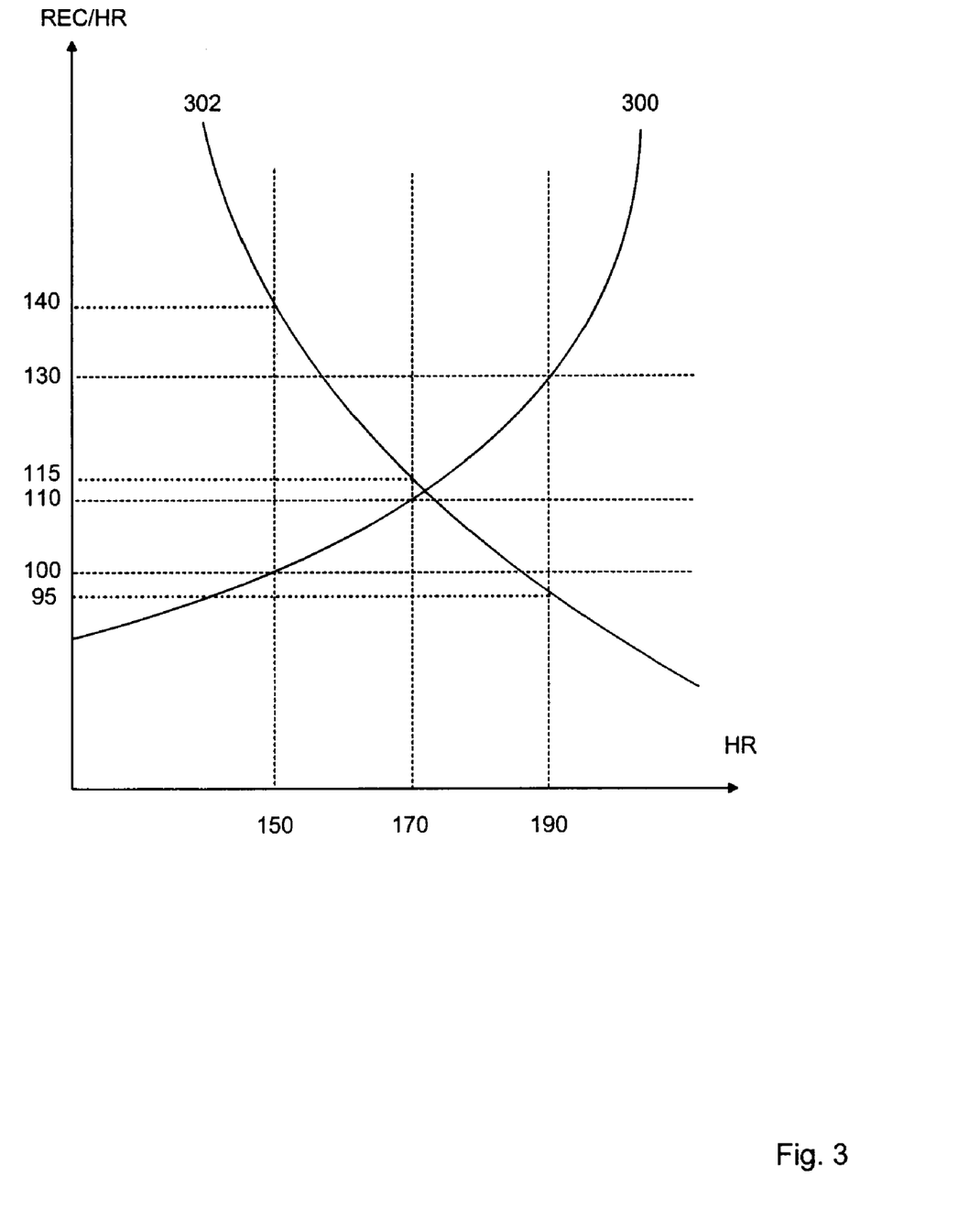
FIG. 3 shows an embodiment of a method.

FIG. 3 shows an embodiment of a relationship 300 for deriving the recovery level shown on the y-axis from the exertion level at the end of the work phase shown on the x-axis. As shown in FIG. 3, the relationship may be an exponentially increasing curve, for instance. In an embodiment of the invention, the curve presents optimal recovery relationship as calculated for a large population of test persons.

If the heart rate of the person is at level 150 at the end of the work phase, the relationship gives the heart rate 100 as the recovery rate. Correspondingly, the recovery rate 110 corresponds to the exertion level 170 and a recovery rate 130 to the exertion level 190. Due to the non-linear relationship of FIG. 3, an equal increase in the exertion level provides a non-equal increase in the recovery rate.

In an embodiment of the invention, the relationship 300 represents one application suitable for strength training. The x-axis may represent the maximum heart rate during an exercise set, while the y-axis may show a targeted recovery heart rate during recovery. When the heart rate during the exercise set (=interval) rises, the recovery heart rate increases. This is due to accumulated fatigue during an exercise session, which both increases the maximum heart rate during intervals and rises the basal heart rate, to which the heart rate may recover.

The relationship 302 presents a case where the intervals are longer in duration, the total work volume is higher, and complete recovery is needed for the next interval. This type of relationship may be used for example in defining work-rest-ratios in the military, for example. The recovery levels 95, 115 and 140 correspond to the respective exertion levels 150, 170 and 190.

Figure 4:
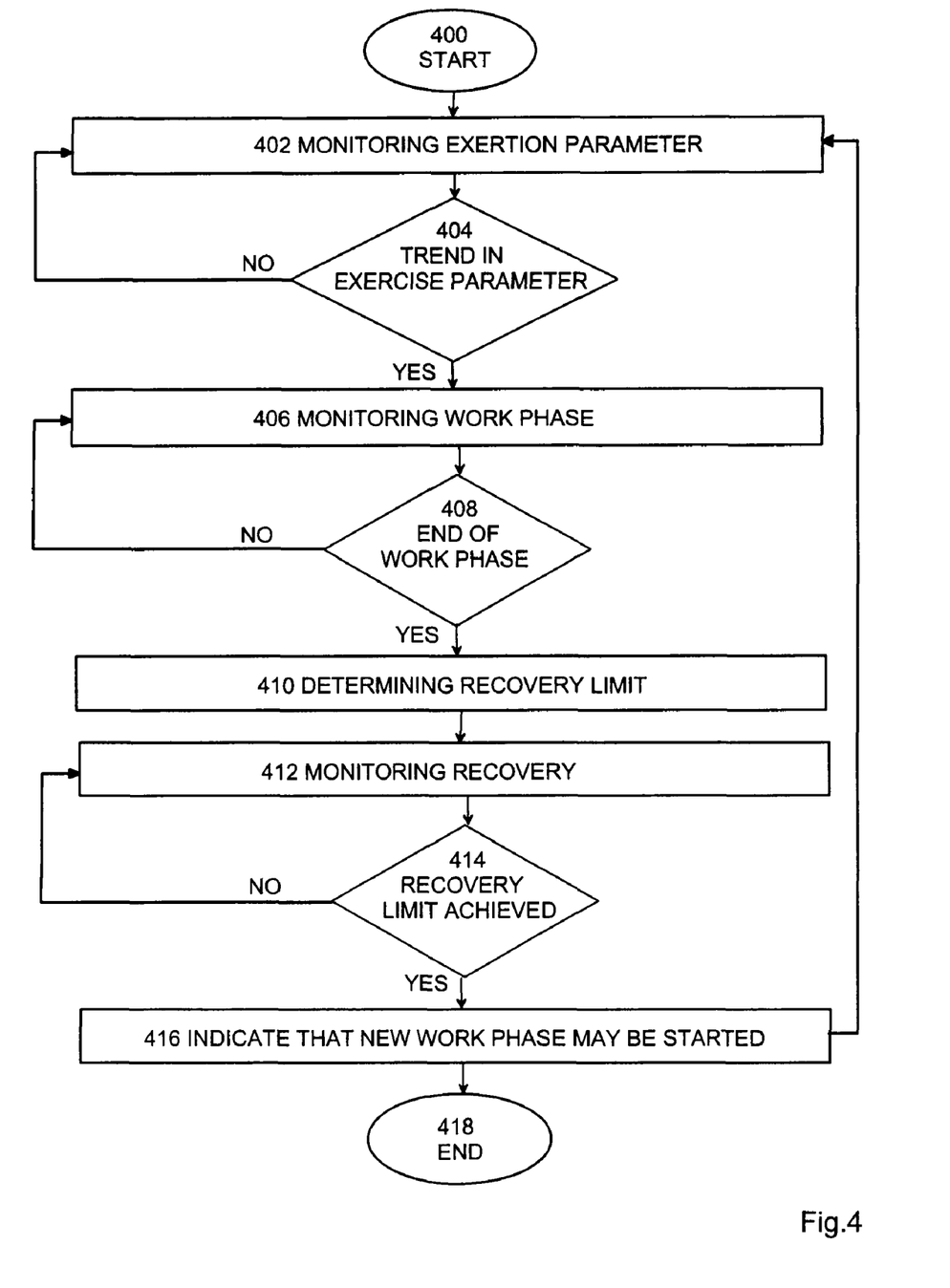
FIG. 4 shows an embodiment of a method.

FIG. 4 shows an embodiment of a method. The method may be applied in conjunction with a fitness exercise. The exercise is an interval exercise including at least two training intervals, where each interval includes a work phase and a recovery phase following the work phase.

The method may be applied to a fitness exercise performed by a healthy person not having any heart disorder, for instance.

The method may be applied online, that is while the person is carrying out the fitness exercise. Alternatively, the method may be applied to stored exercise information usable after the exercise has finished.

In 402, an exercise parameter is monitored. The exertion parameter may be a physiological parameter measured from the user, such as heart rate, heart rate variation, blood pressure, skin temperature or respiration parameter. Alternatively, the exertion parameter may be a training parameter, such as running speed of the person. Furthermore, the exertion parameter may be obtained from an exercise apparatus used by the user and may depict the workload performed by the person.

In 404, it is evaluated if a trend may be found in the exercise parameter data. If the parameter in question is heart rate measured from the person, the trend here is an upward directing trend, that is an increasing heart rate. If the trend is such that the heart rate increases in a predetermined manner, it may be concluded that a work phase has begun. If, for instance, the heart rate parameter data reveals that the heart rate has increased during a time period of ten seconds, this may be a sufficient indication of the beginning of a work phase.

In 406, the work phase is monitored. Here the heart rate may be monitored so as to find the moment of time when the work phase ends. When the person ends the work phase, such as lifting weights, the heart rate may still increase a few seconds, levels off for a short period and starts then to decrease. The aim in 408 is to find the approximate peak in the heart rate. The peak may be a single peak value or an average of a few values around the peak, for instance.

If the peak has been found, the method proceeds to 410, otherwise monitoring of the work phase is continued in 406.

In 410, a recovery limit is determined from the peak level of the heart rate at the end of the work phase. The recovery limit may be calculated by using a predetermined function or read from a lookup table, for instance. The lookup table may store relationships of the values, for example that the recovery level should be set to 135 if the peak heart rate at the end of the work phase is 180, for instance. Corresponding to peak level 190, a recovery level 145 might be set. The lookup table or calculation equation may be personalized to take into account the performance capability, condition or some physiological parameter of the person.

After 410, the method may ensure that a recovery period has really started, which is not shown in FIG. 4 for simplicity. A similar procedure to the one applied in 404 may be used for this purpose. That is, it may be monitored that the heart rate is decreasing for a sufficiently long duration and/or sufficiently much, so that the method may conclude that a recovery period has started. The recovery phase may thereafter be monitored 412.

In 414, it may be checked if the recovery limit has been met. If the recovery level was set to be heart rate 135, in 414 it is checked if the heart rate has sunk to 135. In this way it may be ensured that the recovery from the work phase has been optimal and sufficient for the person.

In 416, in the case of applying the method online to an exercise, an indication may be given to the person that the recovery level has been achieved and a new work phase may be started. The indication may be given to the user by using one or more of a sound, visual or vibration indication, for instance.

The method may then return to 402, 404, where the method then again starts by ensuring that a new work phase has begun. The method may stay in the loop 402 to 416 until the exercise is finished. In an embodiment, the method may also monitor when it would be optimal for the person to finish the exercise. For this purpose, the method may calculate heart rate variation from the user during the exercise. When the heart rate variation has decreased under a predetermined threshold, this may be an indication that the person is sufficiently or too exhausted so that the exercise should be finished. An indication similar to that given in 416 may be then given to the user.

Figure 5:
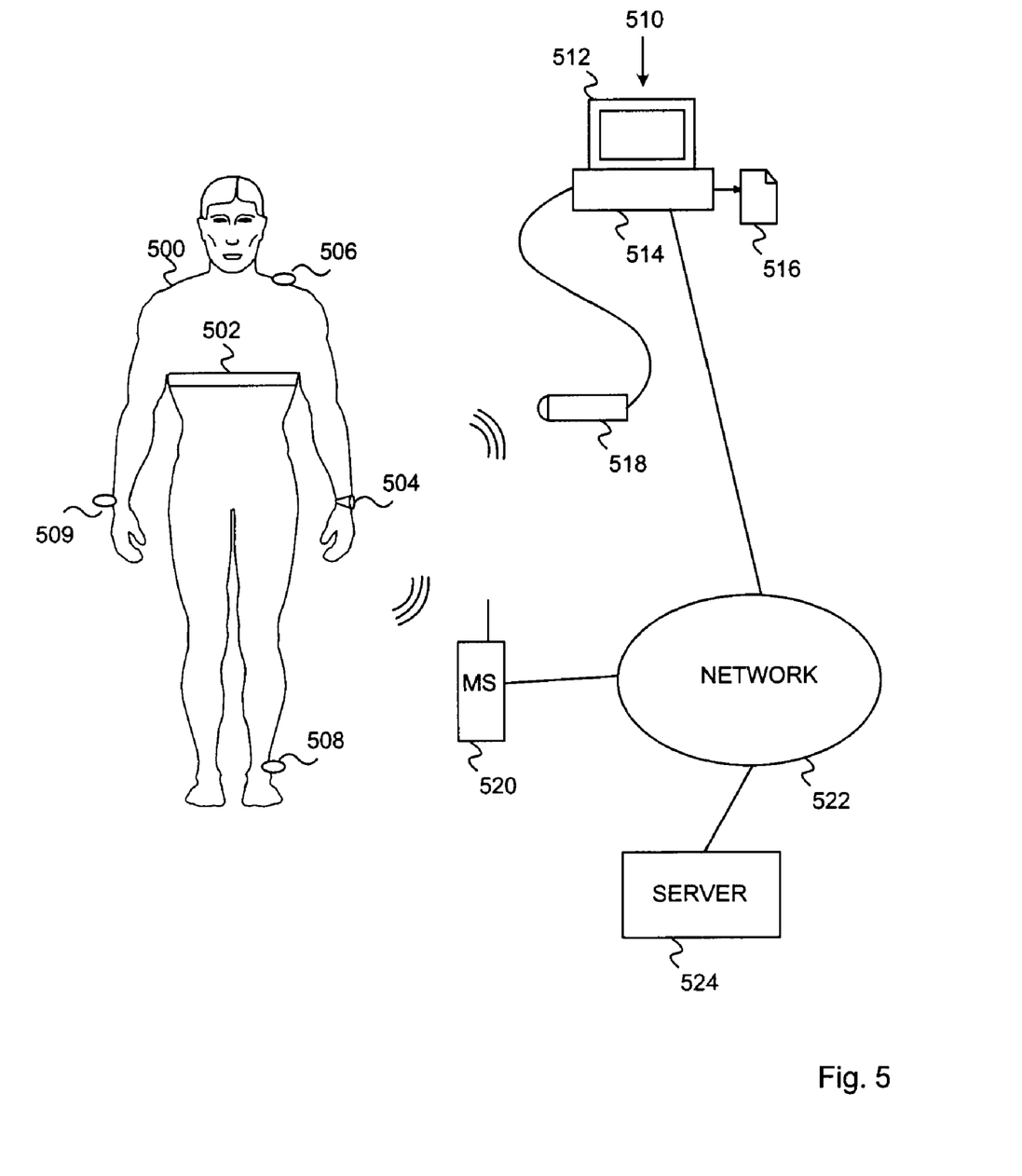
FIG. 5 shows an embodiment of an apparatus.

FIG. 5 shows an embodiment of an apparatus. In the figure, a person 500 who may carry out an interval exercise is shown. In conjunction with the interval exercise, a physiological parameter of the person may be measured. For this purpose, the person 500 is equipped with a performance monitor including an electrode belt 502 for measuring the heart rate from the chest of the person 500, and a wrist-worn receiver device 504 for receiving and displaying the measured heart rate.

Although FIG. 5 shows a two-piece performance monitor including the electrode belt 502 and the wrist-worn device 504, the functionality may be implemented in a one-piece performance monitor as well. The electrode belt 502 on the chest may, in addition to measuring, take care of storing, processing and displaying the heart rate information, and thus the wrist-worn receiver unit 504 is not necessary. The heart rate monitor can also be a single wrist-worn device, in which the heart rate is measured from the wrist either from an ECG signal, arterial pressure pulse or by observing optically changes in the absorption or reflection of blood circulation.

In addition to the physiological parameter, such as heart rate, the activity of the person may be determined. A GPS (Global Positioning System) receiver 506 may receive GPS signals for determining the position of the person 500. Movement of the person may then be determined from the changes in the person's position in time. Movement of the person may also be determined by using a foot pod 508, which calculates the distance walked/run on the basis of the steps taken by the person. Furthermore, an activity monitor 509 may be provided to measure the activity of the person.

Data from one or more of the devices 504, 506, 508, 509 shown may be used to determine the exertion level of the person. In conjunction with an interval exercise, this data may be used to determine events, such as start of a work phase, end of a work phase, exertion level at the end of the work phase, start of a recovery phase, and end of the recovery phase, for instance.

FIG. 5 also shows an external computer 510, which may receive the heart rate data from the performance monitor online during the exercise, or which may receive stored heart rate data after the exercise. Wired or wireless data transmission may be applied between the performance monitor and the computer 510.

The computer 510 may include a display 512, a processing unit 514, a data storage unit 516 and a communication unit 518 for communicating with the performance monitor worn by the user.

If the computer 510 is used in the online mode, it may be operated by a coach of the exercising person, for instance. The computer 510 may plot the exercise variables on the screen, which may show if the recovery phases of the training intervals are adequate with respect to the work phases considering the person's recovery. The computer 510 may then prepare an indication to be sent to the performance monitor, which may then provide a sound and/or visual indication to instruct the person 500 in carrying out the recovery phases.

The computer 510 in FIG. 5 may be situated in an exercising device, such as a treadmill, for instance. The performance monitor used by the person may be equipped with communication equipment/functionality to communicate with the treadmill. The performance monitor may send the heart rate information to the treadmill, which may utilize it in detecting the different phases of the interval training and providing instructions to the person.

The computer 510 may also be used in a post-exercise mode. Then, the performance monitor may store the heart rate information during the interval exercise. The heart rate data may be transferred after the exercise to the computer, where it may be analyzed. The analysis may be visual analysis, for instance, where the display of computer 510 shows for each interval the recovery level and may compare the recovery levels to the actual levels applied by the person. For instance, if the person has not allowed, in a certain interval, his/her heart rate to go sufficiently low, the visual display may indicate this by red color. The same applies if the person has allowed the heart rate to go far too low during the recovery phase. If, however, the person has carried out the recovery phase approximately optimally by starting a new work phase at about the correct moment, the display 512 may be indicate this by using green color, for instance.

FIG. 5 also shows a mobile station 520, which may be wirelessly connected to the performance monitor 504. The mobile station may receive the heart rate data from the performance monitor 504 and communicate the data via a data network 522, such as the Internet, to an external server computer 524. Similarly to the computer 510, the server computer 524 may be connected to the performance monitor online for controlling and/or monitoring the exercise performed by the person.

Therefore, it is clear that the embodiments can be carried out in various devices. To list some embodiments provided by FIG. 5, at least the following ones may be identified. All the functionality may be provided in the performance monitor, one-piece or two-piece, online. In such a case, sound indication, for instance, may be given to the person when a physiological parameter measured from the person has reached the recovery level. In another embodiment, the performance monitor is used in a post-exercise mode. In such a case, the performance monitor stores the heart rate data during the exercise and provides the functionality to analyze the data afterwards.

The combination of the performance monitor and the external computer 510 and/or the server computer 524 may be applied online or in a post-exercise mode as explained above. Here it may be noted that in an embodiment, the performance monitor used by the person includes only the electrode belt. The electrode belt 502 may measure the ECG signal from the person, calculate the heart rate, and send the heart rate information to the computer 510, or to the mobile station 520. The computer may then prepare and give the control information to control the exercise. If the computer is in a treadmill, for instance, the treadmill may give a sound indication when the person should start the next work phase, for instance. Alternatively, the performance monitor only measures the ECG signal and transmits it to an external computer 510 for calculation of the heart rate and carrying out other functionality relating to interval exercises.

Figure 6:
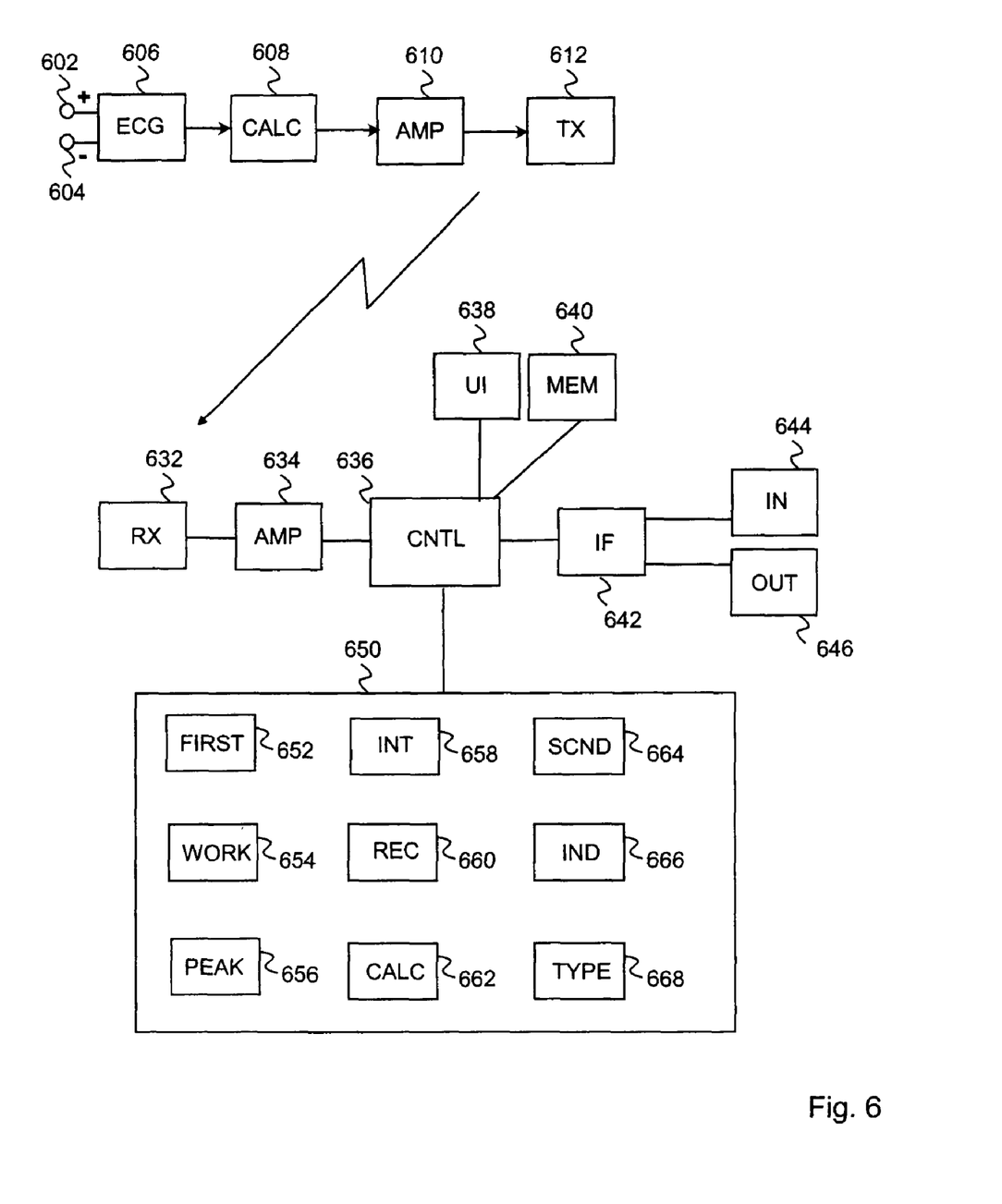
FIG. 6 shows an embodiment of an apparatus.

FIG. 6 shows another embodiment of an apparatus. As explained in the following, the apparatus of FIG. 6 may be placed in a single device or distributed over several devices.

In an embodiment, the devices 602 to 612 are situated in an electrode belt that may be fastened to the chest of a person to measure a physiological parameter from the person. The electrode belt includes at least two electrodes 602, 604 for measuring a potential difference caused by an ECG signal on a person's body. The signal is applied to an ECG preamplifier 606, and may be filtered, after which the heart rate may be calculated. A signal illustrative of the heart rate signal may be amplified in the amplifier 610 before its transmission to an external device, such as wrist-worn device, mobile station, external computer or exercise device. The transmitter 612 may apply inductive or radio transmission, for instance.

The device receiving the heart rate signal may include a receiver 632 for receiving the heart rate signal transmitted using inductive or radio transmission. The signal may be filtered and amplified in the amplifier 634 before forwarding it to a central processor 636, which coordinates the operation of different entities of the receiver.

The device may include a user interface 638. The user interface may include a display for displaying data relevant to operating the device. With regard to an interval exercise, the display may display the heart rate and/or the heart rate variation of the person, a recovery heart rate level, the duration of the exercise, and the number of training intervals, for instance.

The user interface 638 may also include a keyboard. The person may select, by using the keyboard, an interval exercise mode of the device. The device may then carry out functionality that is needed to prepare detection of the different phases of the interval exercise, for instance. By using the keyboard, the exercising person may also select the sports type and the training type. The sports type may be cycling, running or weight lifting, for instance. The training type may be endurance or speed, for instance.

The user interface 638 may further include a sound device. The sound device may provide a sound indication when the person's heart rate has decreased to the recovery level, for instance, so that the person becomes aware of the fact that the next work phase may begin.

The device may also include an interface module 642, which may receive data via a receive module 644 or transmit data via a transmit module 646. Via these interface modules 642 to 646 the device may communicate via further devices. For instance, if the devices 632 to 668 are situated in a wrist-worn performance monitor, the external interfaces may be applied for transmitting heart rate information to an external computer or an exercise device, for instance.

The device may further include an interval exercise module 650, which may include following functional entities. A module 652 for processing first exercise parameter data may be provided. The data may be a physiological parameter measured from the person, an exertion parameter measured from the person's activity or a workout parameter measured by an exercise device, for instance.

The work phase detector 654 may monitor the first exercise parameter data and try to find a work phase therein. The work phase detector 654 may store the requirements for the data to be approved as the beginning of a work phase.

A peak finder 656 may seek a peak in the first exertion parameter data. Basically, the peak finder 656 may try to find the end of the work phase when the first exertion parameter value starts to decrease. At the moment when the peak occurs, the finder 656 may store the peak value or an average of a few values around the peak, for instance.

A calculator 662 may calculate the recovery level of a second exercise parameter on the basis of the peak value of the first exercise parameter. A look up table or a calculation function may be used for this purpose. A type handler 668 may handle the exercise type and/or the sports type. The type may be taken into account when setting the recovery level.

A second exercise parameter data monitor 664 may process data of the second exercise parameter. The second exercise parameter may be a physiological parameter.

A recovery phase detector 660 may detect a recovery phase. The end of the work phase is a first indicator that a recovery phase may have begun. Furthermore, it may be monitored that a period of no work or minor work has been sufficiently long. A decision on the beginning of the work phase may be made on the basis of the first exertion parameter or the second exertion parameter, for instance.

The indicator module 666 may compare the value of the second exercise parameter to the set recovery level of the second exercise parameter. If the second exercise parameter value reaches the threshold value, the indicator may initiate a visual or sound indication to be given to the user.

An interval monitor 658 may receive input information from the user on setting the device into the interval-training mode.

With regard to the device implementation, several alternatives exist for FIG. 6.

All the functionality related to an interval exercise may be implemented in a one-piece performance monitor. In such case, there is no need for transmission modules 612, 632 or interface modules 642 to 646.

If all the interval exercise functionality is implemented in a two-piece performance monitor, the interface modules 642 to 646 are not needed.

The receiver entities 632 to 668 may be, instead of a performance monitor, in a mobile station or an external computer, for instance. The functionality may be distributed over them in many ways.

In an aspect, there is provided an apparatus for an interval exercise performable by a person, the interval exercise including at least two training intervals, each including a work phase and a recovery phase, the apparatus comprising a controller configured to process a first exercise parameter data characterizing an exertion level of the interval exercise. The apparatus comprises a first detector configured to detect a work phase of a training interval from the first exercise parameter data, a second detector configured to detect a value of the first exercise parameter from the exercise parameter data at end of the work phase, and determiner configured to determine a threshold level of a physiological parameter, measured from the person and characterizing the person's recovery level in a recovery phase, based on the value of the first exercise parameter at the end of the work phase.

The apparatus may include one or more elements of a group, comprising a processor usable in an electric device, a performance monitor for monitoring an interval training performed by a healthy person, a mobile station, an external computer connected to a performance monitor and an exercise device.

In an embodiment, the apparatus comprises a second controller configured to process the physiological parameter data, and an indicator configured to provide an indication of the physiological parameter reaching the threshold level of the physiological parameter. The indication may be a sound and/or visual indication, for instance, and may be given by a performance monitor or an exercising device, for instance.

The apparatus may comprise a determiner configured to determine a threshold level of the physiological parameter for each recovery phase separately based on a value of the first exercise parameter at the end of a preceding work phase. That is, a recovery level may be determined for each recovery phase separately depending on the exertion level in the work phase.

The apparatus may comprise a determiner configured to determine a heart rate variation value during at least one recovery phase and an indicator configured to provide an indication if the heart rate variation value goes below a predetermined threshold value. The heart rate variation may be used to determine a suitable moment of finishing the exercise. Disappearance or diminishing of the heart rate variation may be used as an indication of that the person's exertion level has reached a level that the exercise should be finished.

The apparatus according to claim may comprise an interval exercise operation mode, in which the first detector configured to detect a work phase, the second detector configured to detect a value of the first exercise parameter, and the determiner configured to determine a threshold level of a physiological parameter are activated. The person using the performance monitor or the exercising device may activate the operation mode. Alternatively, the device, such as the performance monitor, may enter into the operation mode upon noticing that the character of the exertion parameter data is such that it corresponds to an interval exercise. When the device enters the operation mode, it may take suitable parameter set into use. The parameter set may correspond to one a curve similar to one or those presented in FIG. 3, for instance.

The apparatus may comprises a controller configured to process information of a type of the interval exercise, and a determiner configured to determine the threshold level of the physiological parameter based on the value of the exercise parameter at the end of the work phase and the type of the interval exercise. That is, as shown in FIG. 3, different training types may take different parameter sets or curves into use.

The first exercise parameter characterizes at least one element of a group comprising: motion information of the person, physiological information of the person, and workout information of the person. The motion of the person may be determined by using a GPS receiver or a foot pod, for instance. The physiological information, such as heart rate, may be measured from the person. An exercising device, for instance, may measure the workout information.

The apparatus may comprise an applier configured to apply the threshold level of the physiological parameter in at least one element of a group comprising: controlling the interval exercise, monitoring the interval exercise. The interval exercise may be controlled online, or it may be analyzed afterwards to provide feedback information to the person.

The first exercise parameter may be the physiological parameter measured from the person. That is, the first exercise parameter may be same physiological parameter, such as heart rate that is monitored in the recovery phase.

A method and a computer program product implementing the method and carrying out the functionality of the apparatus may be provided. The embodiments may be implemented by software, hardware, or a combination thereof. The embodiments may be implemented on one or more processors usable in performance monitors, mobile stations, computers or exercise devices, for instance.

The disclosed functionality in various embodiments may be implemented by way of a computer program product encoding a computer program of instructions for executing a computer process of the above-described method. The computer program product may be implemented on a computer program distribution medium. The computer program distribution medium may be any of the known ways of distributing software, such as a computer readable medium, a program storage medium, a record medium, a computer readable memory, a computer readable software distribution package, a computer readable signal, a computer readable telecommunication signal, and a computer readable compressed software package. Alternatively, part of the functionality may be implemented by hardware, such as ASIC (Application Specific Integrated Circuit) or by a combination of hardware and software.

As technology advances, the inventive concept can be implemented in various ways. The invention and its embodiments are not limited to the examples described above but may vary within the scope of the claims.

What is claimed is:

1. An apparatus for an interval exercise performable by a person, the interval exercise including at least two training intervals, each including a work phase and a recovery phase, the apparatus comprising:
   a processing device to process a first exercise parameter data characterizing an exertion level of the interval exercise;
   a detector to detect a work phase of a training interval from the first exercise parameter data;
   a detector to detect a value of the first exercise parameter from the exercise parameter data at the end of the work phase; and
   a determiner to determine a threshold level of a physiological parameter, measured from the person and characterizing the person's recovery level in a recovery phase, based on the value of the first exercise parameter at the end of the work phase.

2. An apparatus according to claim 1, wherein the processing device processes the physiological parameter data, the apparatus further comprising an indicator to indicate the physiological parameter reaching the threshold level of the physiological parameter.

3. An apparatus according to claim 1, the apparatus further comprising a determiner to determine a threshold level of the physiological parameter for each recovery phase separately based on a value of the first exercise parameter at the end of a preceding work phase.

4. An apparatus according to claim 1, the apparatus further comprising: a determiner to determine a heart rate variation value during at least one recovery phase; and
   an indicator to indicate if the heart rate variation value goes below a predetermined threshold value.

5. An apparatus according to claim 1, wherein the apparatus comprises an interval exercise operation mode, in which the detector to detect a work phase, detector to detect a value of the first exercise parameter, and the determiner to determine a threshold level of a physiological parameter are activated.

6. An apparatus according to claim 1, wherein the processing device processes information on a type of the interval exercise, the apparatus further comprising a determiner to determine the threshold level of the physiological parameter based on the value of the exercise parameter at the end of the work phase and the type of the interval exercise.

7. An apparatus according to claim 1, wherein the first exercise parameter characterizes at least one element of a group comprising: motion information on the person, physiological information on the person, and workout information on the person.

8. An apparatus according to claim 1, wherein the apparatus further comprises an applicator to apply the threshold level of the physiological parameter in at least one element of a group comprising: controlling the interval exercise, monitoring the interval exercise.

9. An apparatus according to claim 1, wherein the first exercise parameter is the physiological parameter measured from the person.

10. An apparatus according to claim 1, wherein the apparatus includes one or more elements of a group comprising a processor usable as an electric device, a performance monitor for monitoring interval training performed by a healthy person, a mobile station, an external computer connected to a performance monitor, and an exercise device.

11. An apparatus according to claim 1, the apparatus further comprising:
   means for processing the physiological parameter data; and
   means for providing an indication of the physiological parameter reaching the threshold level of the physiological parameter.

12. An apparatus according to claim 1, the apparatus further comprising means for determining a threshold level of the physiological parameter for each recovery phase separately based on a value of the first exercise parameter at the end of a preceding work phase.

13. An apparatus according to claim 1, the apparatus further comprising
   means for determining a heart rate variation value during at least one recovery phase; and
   means for providing an indication if the heart rate variation value goes below a predetermined threshold value.

14. An apparatus according to claim 1, the apparatus further comprising
   means for processing information on a type of the interval exercise; and
   means for determining the threshold level of the physiological parameter based on the value of the exercise parameter at the end of the work phase and the type of the interval exercise.

15. An apparatus for an interval exercise performable by a person, the interval exercise including at least two training intervals, each including a work phase and a recovery phase, the apparatus comprising:
   means for processing a first exercise parameter data characterizing an exertion level of the interval exercise;
   means for detecting a work phase of a training interval from the first exercise parameter data;
   means for detecting a value of the first exercise parameter from the exercise parameter data at the end of the work phase; and
   means for determining a threshold level of a physiological parameter, measured from the person and characterizing the person's recovery level in a recovery phase, based on the value of the first exercise parameter at the end of the work phase.

* * * * *